(12) United States Patent
Blanchard

(10) Patent No.: US 12,144,938 B2
(45) Date of Patent: Nov. 19, 2024

(54) PRELOADED STYLET VALVE COMPATIBILITY

(71) Applicant: Bard Access Systems, Inc., Salt Lake City, UT (US)

(72) Inventor: Daniel B. Blanchard, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 391 days.

(21) Appl. No.: 17/240,414

(22) Filed: Apr. 26, 2021

(65) Prior Publication Data

US 2021/0330939 A1    Oct. 28, 2021

Related U.S. Application Data

(60) Provisional application No. 63/016,156, filed on Apr. 27, 2020.

(51) Int. Cl.
| | | |
|---|---|---|
| *A61M 25/01* | (2006.01) | |
| *A61M 25/00* | (2006.01) | |
| *A61M 25/06* | (2006.01) | |
| *A61M 39/06* | (2006.01) | |
| *A61M 39/10* | (2006.01) | |
| *A61M 39/22* | (2006.01) | |

(52) U.S. Cl.
CPC .... *A61M 25/0102* (2013.01); *A61M 25/0075* (2013.01); *A61M 25/065* (2013.01); *A61M 39/0693* (2013.01); *A61M 2039/064* (2013.01)

(58) Field of Classification Search
CPC .......... A61M 25/0102; A61M 25/0075; A61M 25/065; A61M 39/0693; A61M 2039/064; A61M 2039/0626; A61M 39/0613; A61M 2039/1072; A61M 39/26; A61M 39/22; A61M 25/0113; A61M 39/10; A61M 25/0021; A61M 25/0043; A61B 17/34
See application file for complete search history.

(56) References Cited

U.S. PATENT DOCUMENTS

2002/0128604 A1\*  9/2002  Nakajima ......... A61M 39/0693
                                                            604/167.04
2012/0172806 A1    7/2012  Woehr et al.
(Continued)

FOREIGN PATENT DOCUMENTS

AU        2018297634 A1    1/2020

OTHER PUBLICATIONS

PCT/US2021/029158 filed Apr. 26, 2021 International Search Report and Written Opinion dated Sep. 1, 2021.

*Primary Examiner* — Robert J Utama
*Assistant Examiner* — Hamza A Darb
(74) *Attorney, Agent, or Firm* — Rutan & Tucker LLP

(57) ABSTRACT

Preloaded catheters are manufactured with a stylet, guidewire, or similar medical device disposed within the catheter, extending through a valve of the connector at a proximal end. During storage and transport, the stylet can remain in place for a prolonged period of time, which can cause stretching, indentations, and damage to the valve faces. These indentations can cause the valve leak, resulting in failure of the device as a whole. Embodiments disclosed herein are directed to devices and methods for preventing contact between the medical device and the valve faces, mitigating damage thereto.

20 Claims, 7 Drawing Sheets

(56) References Cited

U.S. PATENT DOCUMENTS

| | | | |
|---|---|---|---|
| 2014/0163516 A1* | 6/2014 | Lareau | A61B 5/0215 604/247 |
| 2019/0262599 A1* | 8/2019 | Nakagami | A61M 25/0618 |
| 2019/0351210 A1 | 11/2019 | Solomon et al. | |
| 2020/0046938 A1* | 2/2020 | Ma | A61M 25/0097 |
| 2021/0402143 A1* | 12/2021 | Yokota | A61M 39/22 |

* cited by examiner

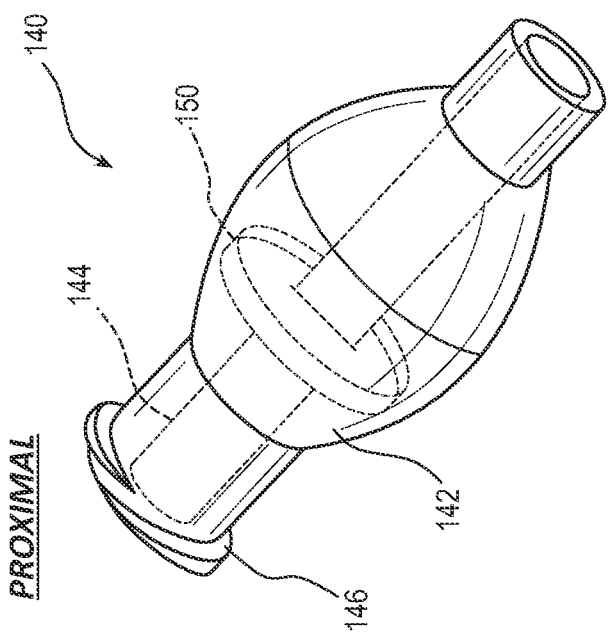
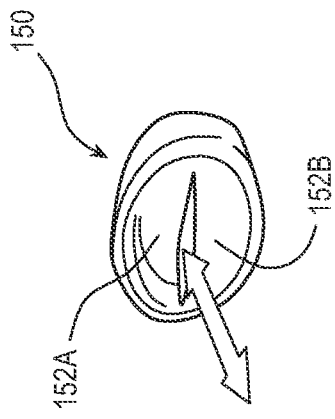
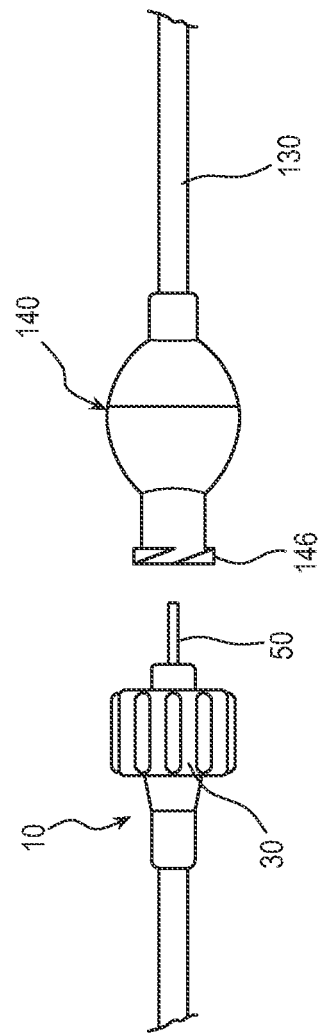
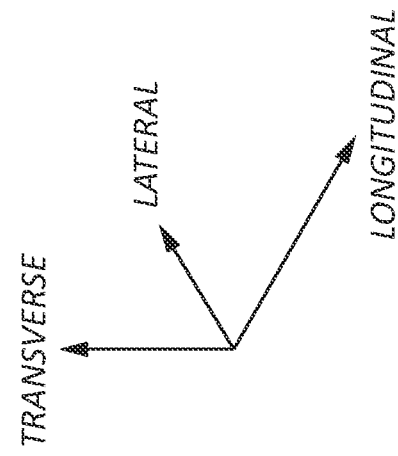
FIG. 2A
FIG. 2B
FIG. 2C

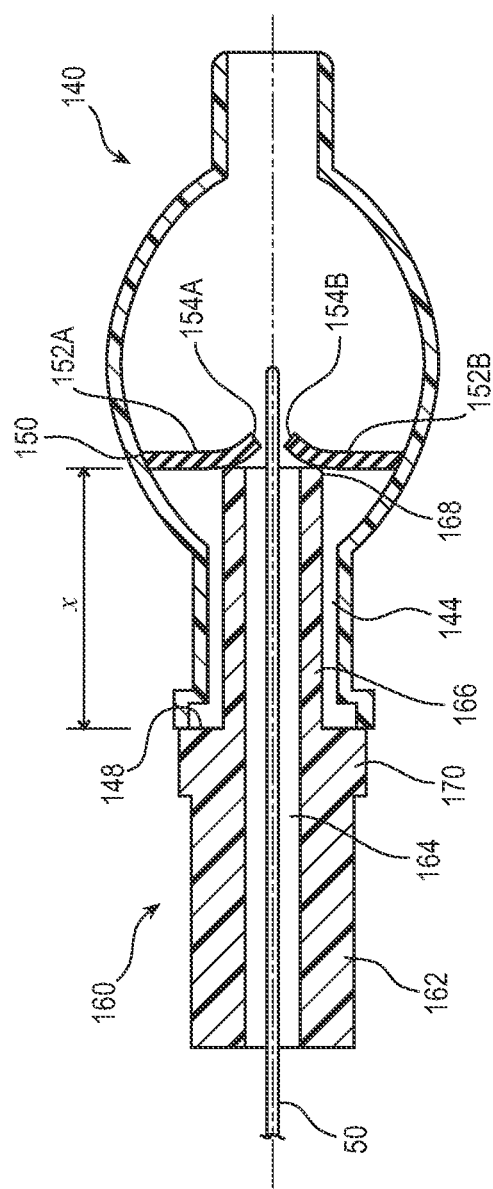
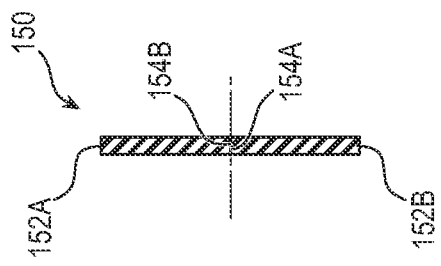
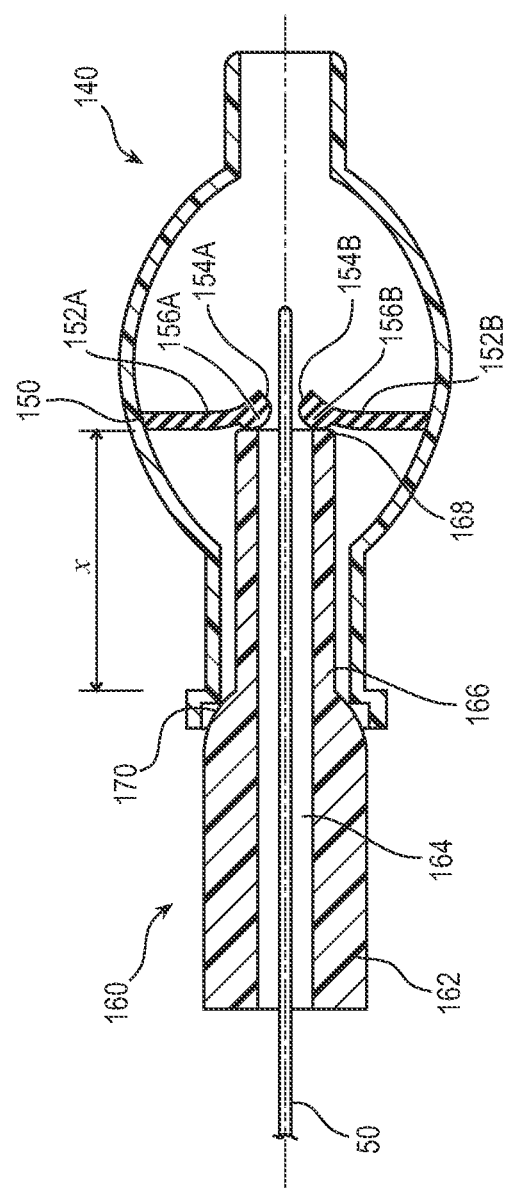

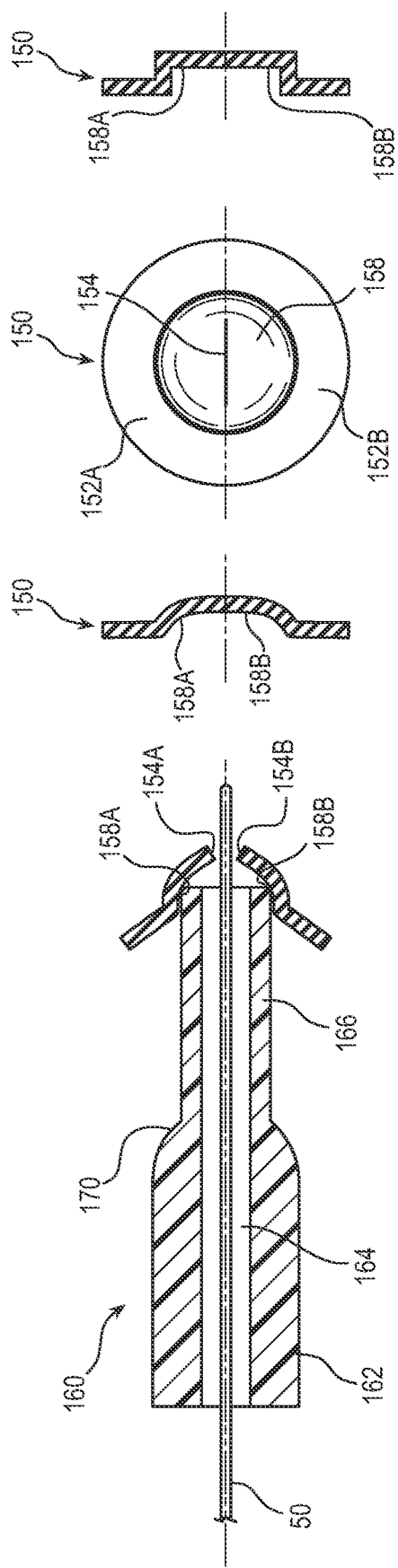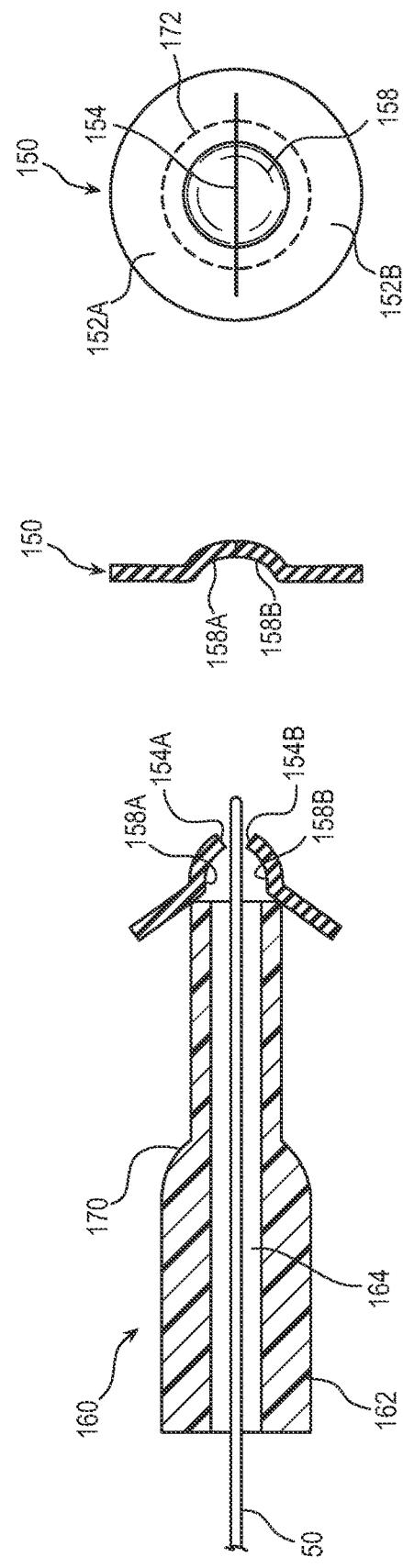

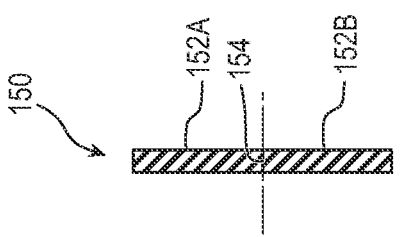
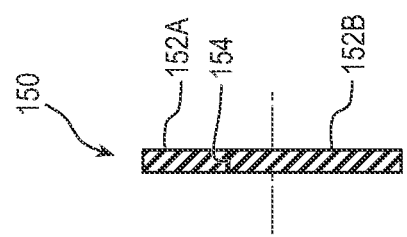
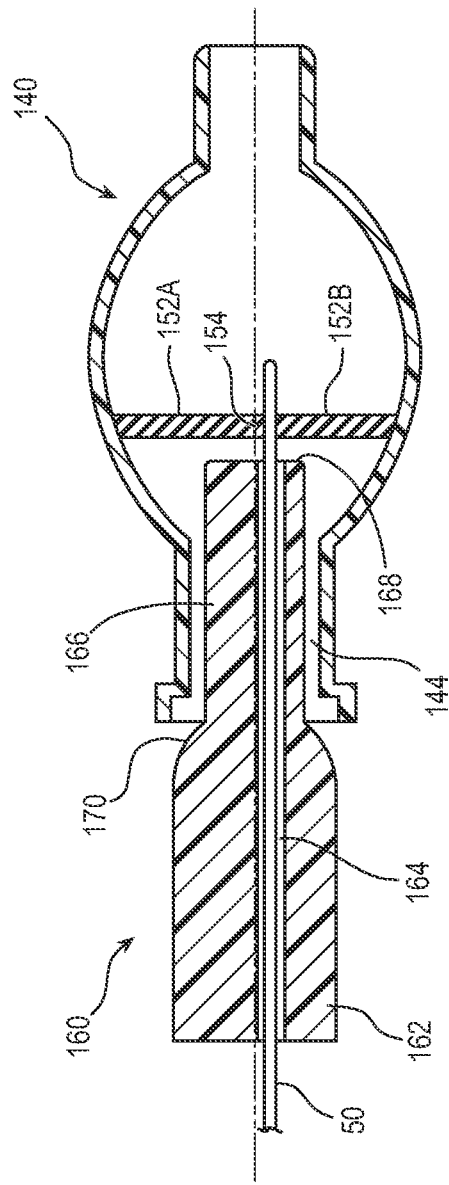
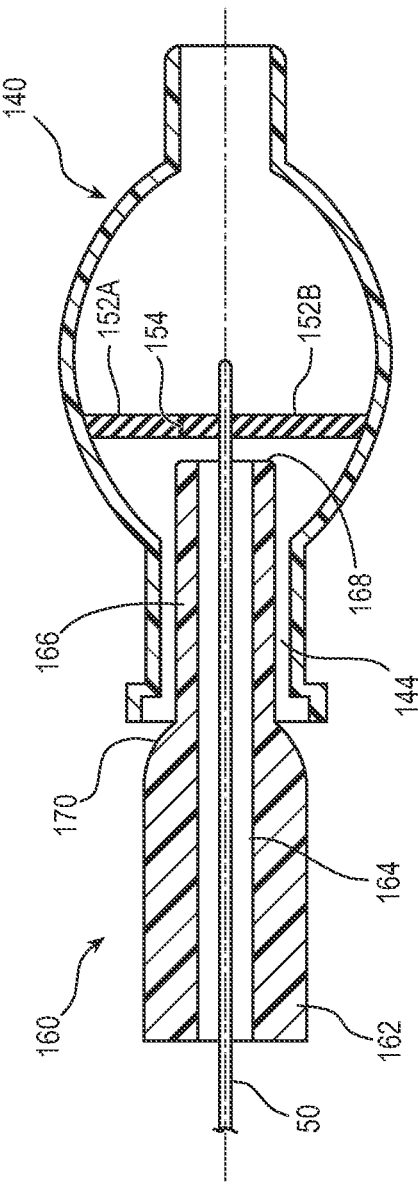

PRELOADED STYLET VALVE COMPATIBILITY

PRIORITY

This application claims the benefit of priority to U.S. Provisional Application No. 63/016,156, filed Apr. 27, 2020, which is incorporated by reference in its entirety into this application.

SUMMARY

Briefly summarized, embodiments disclosed herein are directed to apparatus and methods to allow elongate medical devices, such as stylets and the like, to pass through a valve with little or no impact on the valve function. This is of particular importance during storage and transport of "pre-loaded" catheters and stylets, or for repeated insertions of the medical device over the life span of the valve. Valves such as, for example, those used in catheters and the like often comprise of opposing deformable valve members configured to engage along valve face surfaces to create a seal and inhibit a fluid flow therebetween. The valve members can be deflected to selectively allow fluid to flow, or medical devices to pass therebetween. Where stylets are "pre-loaded" within the catheter and through the valve, the stylet can cause indentations in the valve faces. Over a prolonged period of time, e.g. during transport and storage, the indentations can become permanently set into the valve faces resulting in valve leakage and failure. Alternatively, repeated insertions of medical devices through a valve can also damage the valve face surfaces leading to incomplete sealing and valve failure. Embodiments disclosed herein are directed to devices and methods for preventing contact between the medical device and the valve faces, mitigating damage thereto.

Disclosed herein is a system for introducing a medical device through a valve including, a valve including a first valve member defining a first proximal surface and a first valve face, and a second valve member defining a second proximal surface and a second valve face, the valve configured to transition between a closed configuration and an open configuration, and a valve divider extending from a proximal end to a distal tip and defining a lumen, the distal tip configured to engage the valve and transition the valve from the closed configuration to the open configuration to allow the medical device to pass between the first valve face and the second valve face in a spaced apart relationship.

In some embodiments, the first valve face contacts the second valve face when the valve is in the closed configuration and the first valve face is in a spaced apart relationship from the second valve face when the valve is in the open configuration. One of the first proximal surface and the second proximal surface includes a protrusion that extends proximally and is configured to engage the distal tip of the valve divider. The first proximal surface includes a first cavity and the second proximal surface includes a second cavity, the first cavity and the second cavity co-operate to define a recess in a proximal surface of the valve. A minimum diameter of the recess is larger than an outer diameter of the distal tip, the recess is configured to align the distal tip with a diametric center point of the proximal surface of the valve. In some embodiments, a maximum diameter of the recess is smaller than an outer diameter of the distal tip, and a rim portion of the recess is configured to engage the distal tip. The distal tip of the valve divider remains proximal of the first valve face and the second valve face.

In some embodiments, the valve is disposed within a connector and the valve divider further includes a shoulder portion and a nose portion, the shoulder portion is configured to engage an opening of the connector and the nose portion is configured to extend into the connector a predetermined distance. The connector is disposed at a proximal end of a catheter. The nose portion defines a bi-convex cross sectional shape and is configured to extend between the first valve face and the second valve face. The first valve face and the second valve face are aligned with a central longitudinal axis when in the closed configuration, and an axis of the divider lumen is offset from the central longitudinal axis. The first valve face and the second valve face are offset from a central longitudinal axis when in the closed configuration and an axis of the divider lumen is aligned with the central longitudinal axis. One of the first valve member and the second valve member is formed of a needle penetrable material.

Also disclosed is a valved connector, including, a connector defining a lumen and including a valve including a valve member, the valve configured to control a fluid flow through the lumen of the connector and biased towards to a closed configuration, and a hold-open tab including, a body configured to engage a proximal end of the connector, and an arm extending distally from the body into the connector lumen, a distal tip of the arm releasably attached to the valve member to maintain the valve in an open configuration.

In some embodiments, the hold-open tab is configured to be detached from the valve member to transition the valve to the closed configuration. The body of the hold-open tab defines a lumen that aligns with the connector lumen. In some embodiments, the hold-open tab further includes an elongate medical device extending through the connector lumen to a point distal of the valve, the medical device disposed in a spaced apart relationship from the valve member. The elongate medical device includes one of a stylet, a trocar, a catheter, or an introducer.

Also disclosed is a method of inserting a medical device through a valve including, providing a valve having, a first valve member defining a first proximal surface and a first valve face, and a second valve member defining a second proximal surface and a second valve face, advancing a valve divider until a distal tip thereof contacts one of the first proximal surface and the second proximal surface, transitioning the valve from a closed configuration to an open configuration, and advancing an elongate medical device between the first valve member and the second valve member in a spaced apart relationship from both the first valve face and the second valve face.

In some embodiments, the slit valve is disposed within a connector portion of a catheter. The valve is biased towards a closed configuration. The first valve face contacts the second valve face in the closed configuration to create a seal therebetween, and the first valve face is in a spaced apart relationship from the second valve face in the open configuration to allow a fluid flow therebetween.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 2A shows a perspective view of a connector of the catheter of FIG. 1, in accordance with embodiments disclosed herein.

FIG. 2B shows a side view of a medical line aligned with the exemplary connector of FIG. 2A, in accordance with embodiments disclosed herein.

FIG. 2C shows a perspective view of a valve of the connector of FIG. 2A in an open configuration, in accordance with embodiments disclosed herein.

FIG. 3A shows a cross-section view of a connector including a valve and a valve divider, in accordance with embodiments disclosed herein.

FIG. 3B shows a cross-section view of the valve of FIG. 3A in a closed configuration, in accordance with embodiments disclosed herein.

FIG. 4A shows a cross-section view of a valve and a valve divider, in accordance with embodiments disclosed herein.

FIG. 4B shows a cross-section view of the valve of FIG. 4A in a closed configuration, in accordance with embodiments disclosed herein.

FIG. 5A shows a cross-section view of a valve and a valve divider, in accordance with embodiments disclosed herein.

FIG. 5B shows a cross-section view of the valve of FIG. 5A in a closed configuration, in accordance with embodiments disclosed herein.

FIG. 5C shows a proximal side view of the valve of FIG. 5A in a closed configuration, in accordance with embodiments disclosed herein.

FIG. 5D shows a cross-section view of a valve in a closed configuration, in accordance with embodiments disclosed herein.

FIG. 6A shows a cross-section view of a valve and a valve divider, in accordance with embodiments disclosed herein.

FIG. 6B shows a cross-section view of the valve of FIG. 6A in a closed configuration, in accordance with embodiments disclosed herein.

FIG. 6C shows a proximal side view of the valve of FIG. 6A in a closed configuration, in accordance with embodiments disclosed herein.

FIG. 7A shows a cross-section view of a connector including a valve and a valve divider, in accordance with embodiments disclosed herein.

FIG. 7B shows a cross-section view of the valve of FIG. 7A in a closed configuration, in accordance with embodiments disclosed herein.

FIG. 8A shows a cross-section view of a connector including a valve and a valve divider, in accordance with embodiments disclosed herein.

FIG. 8B shows a cross-section view of the valve of FIG. 8A in a closed configuration, in accordance with embodiments disclosed herein.

DESCRIPTION

Figure 1:
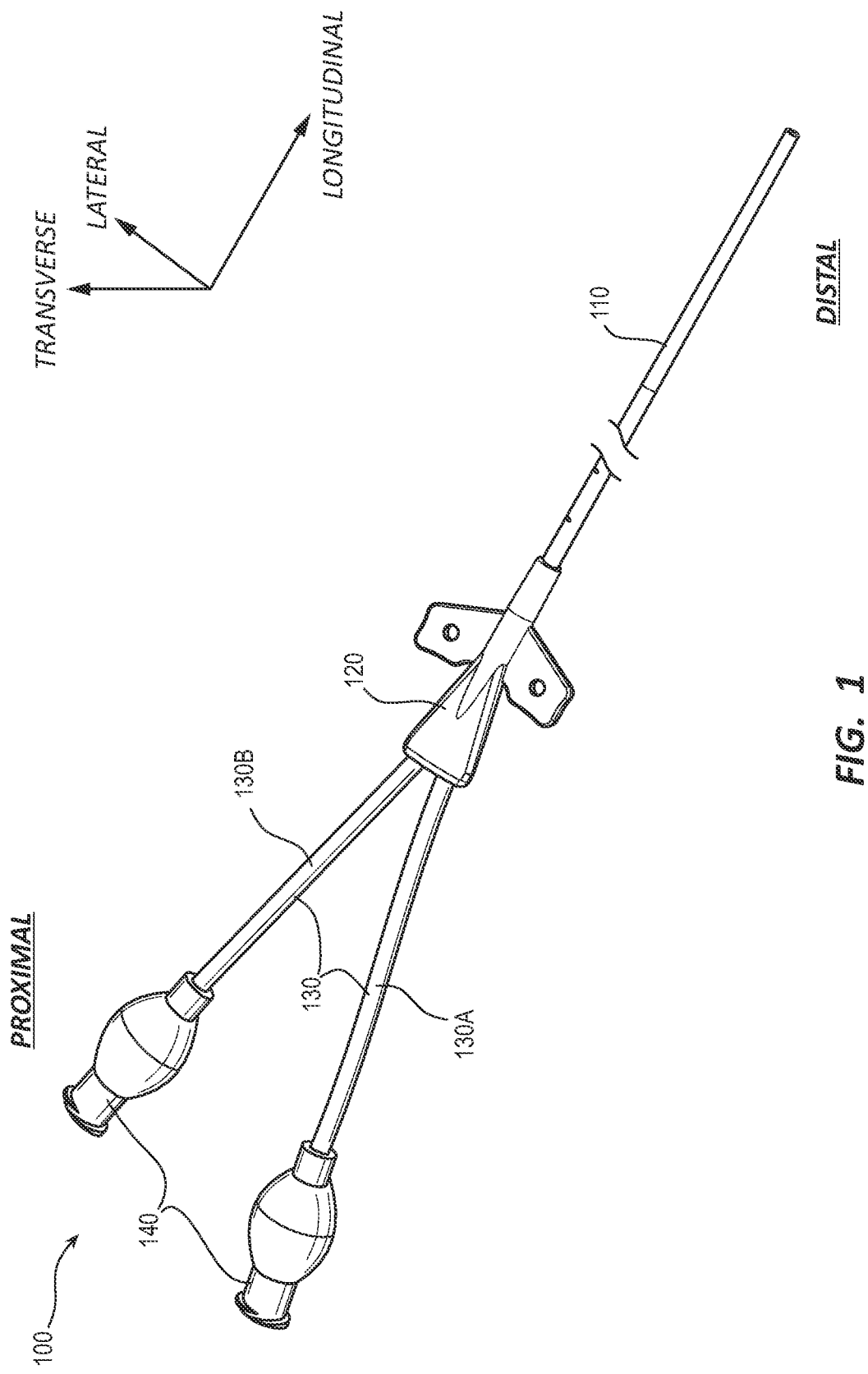
FIG. 1 shows a perspective view of an exemplary catheter, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

To assist in the description of embodiments described herein, as shown in FIGS. 1-2A, a longitudinal axis extends substantially parallel to an axial length of the connector. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

FIG. 1 shows an exemplary catheter system ("catheter") 100. As shown, the exemplary catheter 100 can be a Peripherally Inserted Central Catheter ("PICC"). However, it will be appreciated that embodiments disclosed herein can be used with any catheter or medical device that include valves, such as Central Venous Catheters ("CVC"), intravenous ("IV") catheters, dialysis catheters, midline catheters, introducer sets, port access systems, or the like without limitation.

The catheter 100 generally includes a catheter body 110, defining one or more lumen and supported by a catheter hub 120 coupled to a proximal end thereof. The catheter system 100 can further include an extension leg 130 extending proximally from the hub 120. The extension leg 130 can define an extension leg lumen that is in fluid communication with a lumen of the catheter body 110. It will be appreciated that the catheter system 100 can include two or more extension legs, for example a first extension leg 130A and a second extension leg 130B, each of which are in communication with a lumen of the catheter body 110, e.g. a first extension leg 130A communicates with a first lumen, and a second extension leg 130B communicates with a second lumen. The extension leg 130 can further include a connector 140 disposed at a proximal end thereof.

As shown in FIG. 2A, in an embodiment, the connector 140 includes a body 142 that defines a lumen 144. The lumen 144 extends axially and provides fluid communication between a proximal end to an extension leg 130 disposed a distal end. The connector body 142 can include a coupler 146 disposed at the proximal end of the body 142. The coupler 144 can include a luer lock, spin nut, twist lock, or similar coupling structure configured to secure a medical line, syringe, introducer, or similar device, to the catheter 100. For example, as shown in FIG. 2B, a medical line 10 can be coupled to the connector 140 and secured thereto with a female spin nut 20 configured to engage the coupler 146.

In an embodiment, the connector 140 can include a valve 150 configured to control a fluid flow through the lumen 144 of the connector 140. As shown in FIGS. 2C-3B, in an embodiment, the valve 150 can be a slit valve, however other types of valve including flap valve, duck bill valve, bileaflet, or the like, are also contemplated to fall within the scope of the present invention. It will also be appreciated that the valve can include more than one slit, for example a first slit can be configured to allow a fluid flow in a first direction and a second slit can be configured to allow fluid flow in a second direction, opposite the first. Further, while the valve 150 as shown includes a recessed side surface and defines a substantially oval cross-sectional shape, it will be appreciated that the valve 150 can also include other general cross-sectional shapes such are circular, polygonal, and the like, or surface configurations, such as domed, flat, half-dome, and the like, or combinations thereof. These and similar configurations of valve 150 are contemplated to fall within the scope of the present invention.

As shown in FIG. 2C, the slit valve 150 can be formed of a pliable material, and includes one or more valve members 152, for example a first valve member 152A and a second valve member 152B. In an embodiment, the pliable material can include a polymer, elastomer, rubber, silicone, or similar suitable material. As shown in FIG. 3B, each of the valve members includes a valve face 154 that engages a corresponding valve face of an opposing valve member when in a closed position. For example, the valve 150 includes a normally-closed slit valve including a first valve member 152A defining a first valve face 154A that engages a second valve face 154B of an opposing second valve member 154B when in a closed position.

In an embodiment, the first valve member 152A can engage the second valve member 154B in a closed position to create a seal therebetween and control a fluid flow through the connector lumen 144. The valve members 152A, 152B can transition from the closed configuration (FIG. 3B) to an open configuration (FIG. 3A). In an embodiment, e.g. a "pre-loaded catheter," an elongate medical device, e.g. a stylet 50 can be disposed between the valve members 152 and into the lumen of the catheter 100. The pilable valve members 152 can deform around the outer surface of the stylet 50 to allow the stylet 50 to pass therebetween while preventing a fluid flow therethrough. It will be appreciated that the stylet 50 shown is exemplary and other elongate medical devices are also contemplated including stylets, trocars, catheters, introducers, combinations thereof, and the like.

It will be appreciated that "pre-loaded" catheters can have the stylet 50 disposed between the valve members for a prolonged period of time, during transport and storage. This can result in a permanent indentation in the valve faces 154, as described herein. Further, any movement of the stylet 50, relative to the valve 150, can cause damage to the valve faces 154. The indentations and damage to the valve face 154 can result in leakage, valve failure, and replacement of the entire catheter system 100. Embodiments described herein can maintain a spaced apart relationship between the stylet 50 and the valve face 154 to prevent damage thereto and maintain the integrity of the valve 150.

As shown in FIG. 3A, a valve divider ("divider") 160 is provided. The valve divider 160 can include an elongate body 162 defining a divider lumen 164 extending from a proximal end to a distal end. The valve divider 160 can further include a nose portion 166 disposed at a distal end and configured to be inserted into the lumen 144 of the connector 140 such that a distal tip 168 of the valve divider 160 can contact the valve 150. In an embodiment, the divider lumen 164 can be configured to receive the elongate medical device, e.g. stylet 50, therethrough. In an embodiment, an inner diameter of the divider lumen 164 can be the same, or slightly larger than an outer diameter of the elongate medical device 50, such that the elongate medical device 50 fits snugly therein. In an embodiment, the valve divider 160 can be provided as a separate structure. In an embodiment, the valve divider 160 can be provided as part of a medical line 10, coupler 30, or other device that can be coupled to the connector 140, or combinations thereof.

As shown in FIG. 3A, in an embodiment, the nose portion 166 can be inserted into the connector lumen 144 and a distal tip 168 can contact the valve members 152. The valve divider 160 can be urged distally to slightly deflect the valve members 152, separating the valve faces 154, and create an opening therebetween. The stylet 50 can be disposed, through the opening in a spaced apart relationship from the valve faces 154. In an embodiment, the valve divider 160 remains in place to prevent any contact between the stylet 50 and the valve faces 154. Advantageously, neither the valve divider 160, nor the stylet 50 contacts the valve faces 154, thereby maintaining the integrity of the valve 150. In an embodiment, the valve divider 160 can be used to deflect the valve members 152 when the stylet is being moved relative to the catheter to prevent damaging the valve faces 154. When the catheter 100 is placed correctly, the stylet 50 can be removed. The valve divider 160 can then be removed to allow the valve to resume the normally-closed configuration.

In an embodiment, the valve divider 160 can include a shoulder portion 170, disposed between the nose portion 166 and the body 162. A distance (x) between the shoulder portion 170 and the distal tip 168 can be a predetermined length. As such, the shoulder portion 170 can engage an opening 148 of the connector lumen 144 and the distal tip 168 can extend into the connector lumen 144 a predetermined distance (x). The predetermined distance (x) can be sufficient to deform the valve members 152 to create an opening, as described herein, without stretching or damaging the valve members 152. In an embodiment, as shown for example in FIG. 3A, the shoulder portion 170 can define a surface extending perpendicular to the longitudinal axis and is configured to engage an opening 148 of the connector 140. In an embodiment, as shown for example in FIG. 4A, the shoulder portion 170 can define a curved cross sectional profile, or a frusto-conical profile, to engage the opening 148 and align the valve divider with an axial center line of the connector lumen 144. In an embodiment, the valve divider 160 includes a female coupler, configured to engage the coupler 146 of the connector 140 and configured such that the distal tip 168 of the valve divider 160 extends into the connector lumen 144 a predetermined distance (x).

In an embodiment, as shown in FIGS. 4A-4B, the valve member 152 can include a protrusion 156, for example a first valve protrusion 156A and a second valve protrusion 156B. FIG. 4A shows the valve members in an open configuration. FIG. 4B shows the valve members 152 in a closed configuration. The valve protrusion 156 can extend proximally from a side surface of the valve member 152 and can define a hemi-spherical shape. However, it will be appreciated that other three-dimensional shapes are also contemplated to fall within the scope of the present invention. As shown in FIG. 4A, the protrusions 156 provide a contact surface that the distal tip 168 of the valve divider 160 can abut against and separate the valve faces 154, as described herein. Advantageously, the protrusion 156 can provide a thickened portion to provide a stand-off between the distal tip 168 and the valve face 154 to reduce wear or damage on the valve member 152 and/or valve face 154 from repeated engagements with the distal tip 168 of the valve divider 160. Advantageously, the longitudinal extension of the protrusion 156 provides a lever that facilitates rotation of the valve face 154 away from the surface of the stylet 50, to create an opening. To note, for clarity, FIGS. 4A-6C only show embodiments of the valve divider 160 and the valve 150.

In an embodiment, as shown in FIGS. 5A-5C, the valve members 152 can include a concave cavity or recess 158. For example, a first valve member 152A includes a first cavity 158A, and a second valve member 152B includes a second cavity 158B. FIG. 5A shows a cross section view of the valve members 152 in an open configuration. FIG. 5B shows a cross section view of the valve members 152 in a closed configuration. FIG. 5C shows a proximal side view of the valve members 152 in a closed configuration. As shown in FIG. 5C, when the valve 150 is in the closed configuration, the first cavity 158A and the second cavity 158B can co-operate to form a concave recess 158. As shown, the first cavity 158A and the second cavity 158B can be semi-circular and co-operate to for a substantially circular recess 158. However, it will be appreciated that this is exemplary and that one of the first cavity 158A, the second cavity 158B, or the recess 158 can define an oval, elliptical, polygonal, rectangular, or any closed curve regular or irregular polygonal shape. Further, the first cavity 158A and the second cavity 158B can be the same shape, can be "mirror-image" shapes of each other, or can be asymmetrical shapes, and still co-operate to form recess 158.

In an embodiment, the recess 158 can extend over a portion of the side surface of the valve 150. In an embodiment, the recess 158 can extend over substantially the entire side surface of the valve 150. In an embodiment, the recess 158 can encircle a portion of the valve slit 154 defined by valve faces 154A, 154B, e.g. FIG. 6C. In an embodiment, the recess 158 can encircle the entire slit 154 of the slit valve such that the length of the valve faces 154A, 154B are disposed within the recess 158, e.g. 5C. In an embodiment, a minimum diameter of the recess 158 is the same or slightly larger than an outer diameter of the distal tip 168 of the valve divider 160, such that the distal tip 168 can fit therein in. In an embodiment, as shown for example in FIG. 5D, a perimeter surface of the recess 158 can extend substantially parallel to the longitudinal axis. In an embodiment, as shown for example in FIGS. 5A-5B a perimeter surface of the recess 158 can be chamfered or rounded to facilitate guiding the distal tip 168 towards a diametric center point of the proximal side of the valve 150. (FIG. 5A.) Advantageously, the recess 158 can provide a receiving structure configured to receive the distal tip 168 of the valve divider 160 and align the divider lumen 164, and any elongate medical device 50, disposed therein, with a diametric center point of the valve 150. As such, when the valve divider is inserted into the connector 140 to separate the valve faces 154, as described herein, the recess can align the valve divider 160 and the stylet 50 with the opening so that the stylet 50 passes through the opening without touching the valve faces 154.

As shown in FIGS. 6A-6C, in an embodiment, a maximum diameter of the recess 158 can be less than an outer diameter of the distal tip 168. As such the distal tip 168 contacts the valve member 152 at a rim portion 172 of the recess 158. Advantageously, the rim portion 172 is disposed proximally of the diametric center point and provides a stand-off between the distal tip 168 and the valve face 154. In an embodiment, the valve member 152 includes two or more recessed portions, a first recess portion can define a diameter that is the same or slightly larger than the outer diameter of the distal tip 168, as described herein (FIGS. 5A-5C), and a second recessed portion can define a diameter that is less than the outer diameter of the distal tip 168, as described herein (FIGS. 6A-6C).

As shown in FIGS. 7A-7B, in an embodiment, the valve members 152 can be arranged symmetrically such that the valve faces 154A, 154B engage along a central axis. In an embodiment, the valve divider 160 includes an offset lumen 164 that is axially offset from the central axis. As such, the stylet 50, inserted through the offset lumen 164 can be aligned with the valve member 152 away from the valve face 154. In an embodiment, the valve member 152 can be formed of a penetrable silicone rubber, or the like. As such the stylet 50 can be inserted through the valve member 152, away from the valve face 154 and avoid damaging the valve face 154. The valve member 152 can be configured to sustain multiple penetrations without compromising the integrity of the valve barrier or the flexible function of the valve member 152.

As shown in FIGS. 8A-8B, in an embodiment, the valve members 152 can be arranged in an asymmetrical configuration, such that the valve faces 154A, 154B engage at an offset positon relative to the central axis. In an embodiment, the valve divider 160 includes a centrally disposed lumen 164 that is axially aligned with the central axis. As such, the stylet 50, inserted through the lumen 164 can be aligned with the valve member 152 away from the valve face 154. As described herein, the valve member 152 can be formed of a penetrable silicone rubber, or the like. As such, the stylet 50 can be inserted through the valve member 152, away from the valve face 154 and avoid damaging the valve face 154. The valve member 152 can be configured to sustain multiple penetrations without compromising the integrity of the valve barrier or the flexible function of the valve member 152.

Figure 9A:
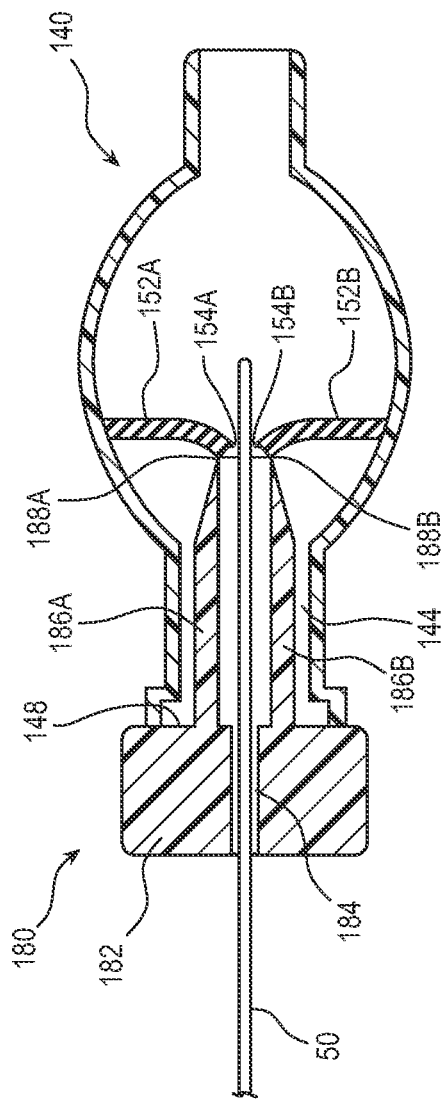
FIG. 9A shows a cross-section view of a connector including a valve and a hold-open tab attached to the valve, in accordance with embodiments disclosed herein.
Figure 9B:
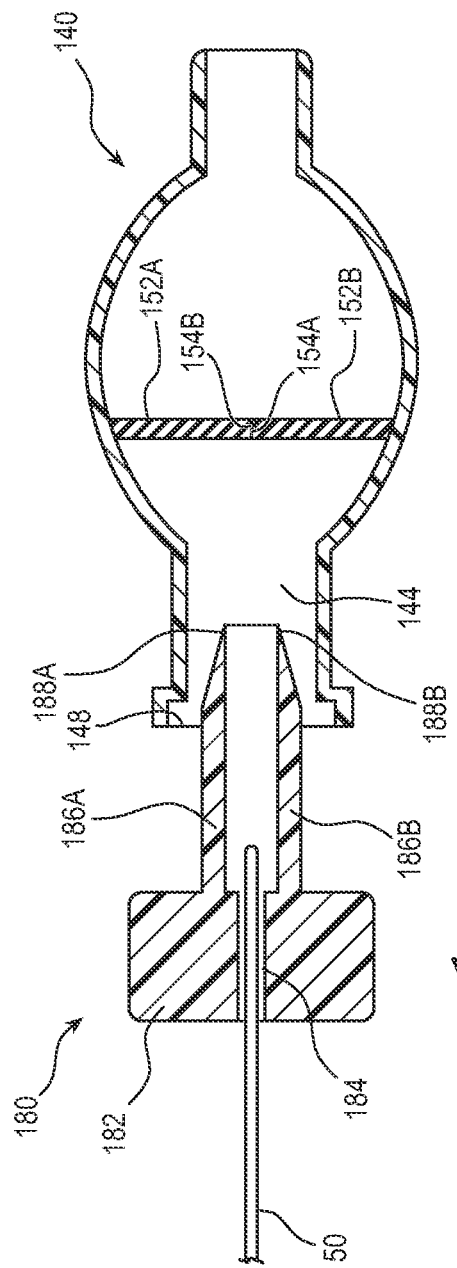
FIG. 9B shows a cross-section view of a connector including a valve and a hold-open tab detached from the valve, in accordance with embodiments disclosed herein.

As shown in FIGS. 9A-9B, in an embodiment, the connector 140 can include a hold-open tab ("tab") 180. The hold-open tab 180 includes a body 182, which includes a width that is greater than a diameter of the lumen opening 148 of the connector 140 to prevent the body 182 from advancing into the lumen 144. In an embodiment, the body 182 includes a female coupler configured to engage the coupler 146 of the connector 140. The tab 180 can further include a first arm 186A and a second arm 186B, each extending distally from the body 182 into the lumen 144. A distal tip 188 can be releasably attached to a portion of the valve member 152 to hold the valve member 152 in an open configuration. As shown, the distal tip 188 is coupled to an intersection between the valve face 154 and the side surface, however it will be appreciated that this is exemplary and the arm 186 can be coupled to any portion of the valve member 152.

In an embodiment, the distal tip 188 can be attached to the valve member 152 with adhesive, bonding, ultrasonic welding, combinations thereof or the like. In an embodiment, the arm 186 and the valve member 152 can be formed as a single unitary piece and include a breach line disposed substantially at the distal tip 188. The breach line can include a score line, perforation, laser cut line, or similar line of weakness configured to facilitate separation of the tab 180 from the valve 150 when the tab 180 is urged proximally. In an embodiment, the distal tip 188 is releasably coupled to the valve member 152 with a frangible bridge, or similar frangible structure that can facilitate separation of the tab 180 from the valve 150 when the tab 180 is urged proximally.

As shown in FIG. 9A, in an embodiment, the hold-open tab 180 can maintain the valve members 152 in an open configuration. A stylet can then be disposed through the tab lumen 184, through the connector lumen 144 and through the opening between the valve faces 154. Once the catheter 100 has been placed, the stylet 50 can be removed. As shown in FIG. 9B, the hold-open tab 180 can then be withdrawn proximally which separates the first distal tip 188A from the first valve member 152 and the second distal tip 188B from the second valve member 152B, allowing the valve members to transition to the closed configuration. The hold-open tab 180 can be removed and discarded. Advantageously, the hold-open tab 180 can be positioned during manufacture of a "pre-loaded" catheter and remain in place during storage and transport to prevent permanent indentations forming in the valve faces 154.

Figure 10B:
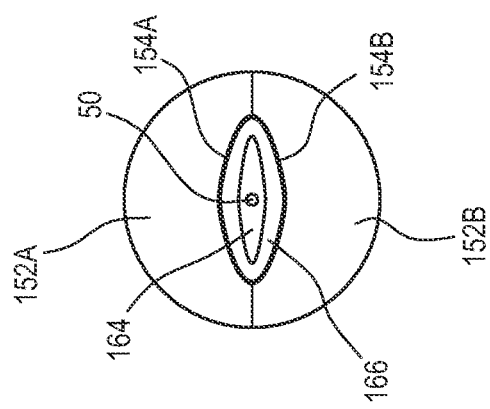
FIG. 10B shows a lateral cross-section view of a connector including a valve and a valve divider, in accordance with embodiments disclosed herein.
Figure 10A:
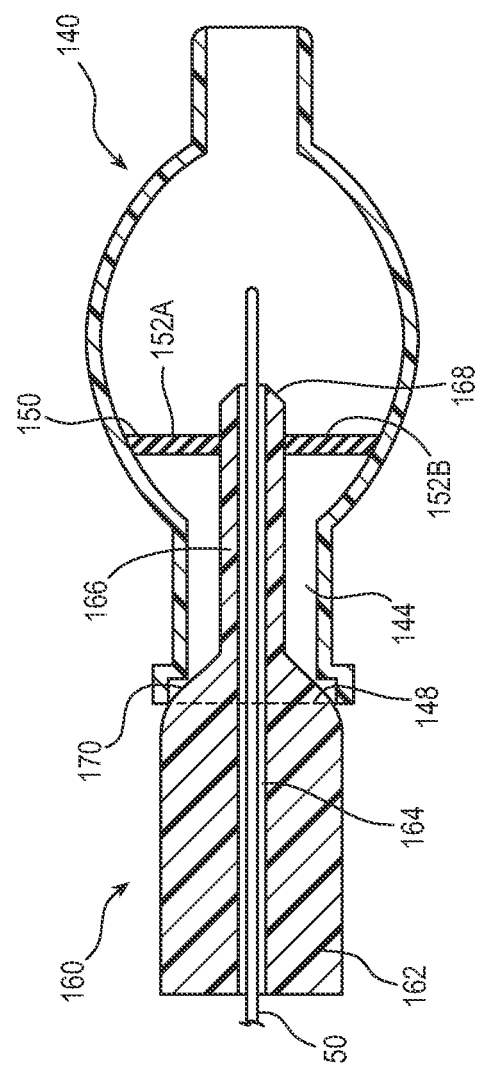
FIG. 10A shows a longitudinal cross-section view of a connector including a valve and a valve divider, in accordance with embodiments disclosed herein.

As shown in FIGS. 10A-10B, in an embodiment, the nose portion 166 of the valve divider 160 defines a bi-convex cross-sectional shape with a lateral width that is greater than a transverse height. In an embodiment, a distal tip 168 can include a chamfered edge. In an embodiment, the nose portion 166 can be inserted between the valve faces 154. As shown in FIG. 10B, the bi-convex cross-sectional shape can distribute the pressure across the entire valve face 154, preventing any indentation forming in the valve face 154 during prolonged storage or transport.

In an exemplary method of use, a valve divider 160 is provided as described herein, and including an elongate medical device, such as a stylet 50, disposed therethrough. The nose portion 166 of the valve divider 160 can be inserted into a lumen 144 of a connector 140 until a distal tip thereof abuts against a valve member, transitioning the valve from a closed configuration to an open configuration where the valve faces 154 are separated, creating an opening. The stylet 50 can then be advanced distally through the lumen 164 of the valve divider 160, between the valve faces 154 in a spaced apart relationship from the valve faces 154.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A system for introducing a medical device, comprising:
a valve including a first valve member defining a first proximal surface and a first valve face, and a second valve member defining a second proximal surface and a second valve face, the valve configured to transition between a closed configuration and an open configuration; and
a valve divider extending from a proximal end to a distal tip and defining a divider lumen, the distal tip releasably attached to one or both of the first proximal surface and the second proximal surface of the valve to deflect one or both of the first valve member and the second valve member in a proximal direction and maintain the valve in the open configuration to allow the medical device to pass between the first valve face and the second valve face in a spaced apart relationship.

2. The system according to claim 1, wherein the first valve face contacts the second valve face when the valve is in the closed configuration and the first valve face is in a spaced apart relationship from the second valve face when the valve is in the open configuration.

3. The system according to claim 1, wherein the first proximal surface includes a first cavity and the second proximal surface includes a second cavity, the first cavity and the second cavity co-operate to define a recess in a proximal surface of the valve.

4. The system according to claim 1, wherein a first portion of the distal tip is releasably attached to the first proximal surface of the first valve member and a second portion of the distal tip is releasably attached to the second proximal surface of the second valve member.

5. The system according to claim 1, wherein the distal tip is releasably attached to one or both of the first proximal surface and the second proximal surface of the valve by a frangible bridge.

6. The system according to claim 1, wherein the distal tip of the valve divider remains proximal of the first valve face and the second valve face.

7. The system according to claim 1, wherein the valve is disposed within a connector and the valve divider further includes a shoulder portion and a nose portion, the shoulder portion is configured to engage an opening of the connector and the nose portion is configured to extend into the connector a predetermined distance.

8. The system according to claim 7, wherein the connector is disposed at a proximal end of a catheter.

9. The system according to claim 1, wherein the valve divider is configured to be detached from one or both of the first valve member or the second valve member to transition the valve to the closed configuration.

10. The system according to claim 1, wherein the first valve face and the second valve face are aligned with a central longitudinal axis when in the closed configuration, and an axis of the divider lumen is aligned with the central longitudinal axis.

11. The system according to claim 1, wherein one of the first valve member and the second valve member is formed of a needle penetrable material.

12. A valved connector, comprising:
   a connector defining a connector lumen and including a valve including a valve member, the valve configured to control a fluid flow through the connector lumen and biased toward a closed configuration; and
   a hold-open tab comprising:
      a body configured to engage a proximal end of the connector; and
      an arm extending distally from the body into the connector lumen, a distal tip of the arm releasably attached to the valve member to deflect the valve member in a proximal direction and maintain the valve in an open configuration.

13. The valved connector according to claim 12, wherein the hold-open tab is configured to be detached from the valve member to transition the valve to the closed configuration.

14. The valved connector according to claim 12, wherein the body of the hold-open tab defines a lumen that aligns with the connector lumen.

15. The valved connector according to claim 12, further including an elongate medical device extending through the connector lumen to a point distal of the valve, the elongate medical device disposed in a spaced apart relationship from the valve member.

16. The valved connector according to claim 15, wherein the elongate medical device includes one of a stylet, a trocar, a catheter, or an introducer.

17. A method of inserting a medical device through a valve of a connector, comprising:
   providing a first valve member defining a first proximal surface and a first valve face, and a second valve member defining a second proximal surface and a second valve face, a hold-open tab having a body engaging a proximal end of the connector, and an arm extending distally from the body into a connector lumen, a distal tip of the arm releasably attached to one of the first valve member or the second valve member to deflect the first valve member or the second valve member in a proximal direction and maintain the valve in an open configuration; and
   advancing an elongate medical device between the first valve member and the second valve member in a spaced apart relationship from both the first valve face and the second valve face.

18. The method according to claim 17, further including urging the hold-open tab proximally relative to the connector to detach the arm from one of the first valve member and the second valve member.

19. The method according to claim 17, wherein the valve is biased toward a closed configuration.

20. The method according to claim 19, wherein the first valve face contacts the second valve face in the closed configuration to create a fluid tight seal therebetween, and the first valve face is in the spaced apart relationship from the second valve face in the open configuration to allow a fluid flow therebetween.

* * * * *